US00PP15106P2

(12) United States Plant Patent
Olesen et al.

(10) Patent No.: US PP15,106 P2
(45) Date of Patent: Aug. 24, 2004

(54) ROSE PLANET NAMED 'POULYC003'

(50) Latin Name: *Rosa hybrida*
Varietal Denomination: POULyc003

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 5 days.

(21) Appl. No.: 10/719,710

(22) Filed: Nov. 21, 2003

(51) Int. Cl.[7] ..... A01H 5/00
(52) U.S. Cl. ..... Plt./111
(58) Field of Search ..... Plt./111

*Primary Examiner*—Anne Marie Grunberg
*Assistant Examiner*—S B McCormick-Ewoldt

(57) ABSTRACT

A new climbing garden rose plant which has abundant, apricot-yellow blend flowers and attractive foliage. This new and distinct variety has shown to be uniform and stable in the resulting generations from asexual propagation.

1 Drawing Sheet

Botanical classification: *Rosa hybrida.*
Variety denomination: 'POULyc003'.

SUMMARY OF THE INVENTION

The present invention constitutes a new and distinct variety of garden rose plant which originated from a controlled crossing between a female parent 'MEIdomonac', and the unnamed male parent. The two parents were crossed during the summer of 1991, and the resulting seeds were planted in a controlled environment in Fredensborg, Denmark. The new variety is named 'POULyc003'.

The new variety may be distinguished from its seed parent, 'MEIdomonac', by the following combination of characteristics:

1. The seed parent has Red Group 55C colored petals while the applicant variety has Yellow Group 10D colored petals.
2. The seed parent is suitable for growing as a landscape shrub variety while the applicant variety is suitable for growing as a climbing variety.

The new variety may be distinguished from its unnamed pollen parent, by the following combination of characteristics:

1. The pollen parent has orange-blend colored petals while the applicant variety has apricot-yellow blend colored petals.
2. The pollen parent has shorter growth habit than the applicant variety.

The objective of the hybridization of this rose variety was to create a new and distinct variety for garden use with unique qualities, such as:

1. Uniform and abundant apricot-yellow blend flowers;
2. Vigorous, but compact growth when propagated both as a budded rose and on its own roots;
3. Disease resistance.
4. Improved flowering habit. Since the vqariety is less apically dominant, flowers are produced from lower branches to the top.

This combination of qualities is not present in previously available commercial cultivars of this type, known to the inventor, and distinguish 'POULyc003' from all other varieties of which we are aware.

As part of their rose development program, L. Pernille Olesen and Mogens N. Olesen germinated the seeds from the aforementioned hybridization during winter 1991 and conducted evaluations on the resulting seedlings in a controlled environment in Fredensborg, Denmark.

'POULyc003' was selected in the spring 1992 by the inventors as a single plant from the progeny of the aforementioned hybridization.

Asexual reproduction of 'POULyc003' by traditional budding and rooted cuttings was first done by L. Pernille and Mogens N. Olesen in their nursery in Fredensborg, Denmark in June, 1992. This initial and other subsequent asexual propagations conducted in controlled environments have demonstrated that the characteristics of 'POULyc003' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULyc003'. Specifically illustrated in FIG. 1:

FIG. 1.1; Stem showing open flower, the attachment of buds, and peduncles;

FIG. 1.2; Flower bud closed and partially open;

FIG. 1.3; Flower petals, detached;

FIG. 1.4; Sepals, receptacle, and pedicel;

FIG. 1.5; Mature leaves and bare stem;

FIG. 1.6; Juvenile leaves attached to stem and bare stem.

DETAILED DESCRIPTION OF THE VARIETY

Figures 11, 12, 13, 14, 15, 16:
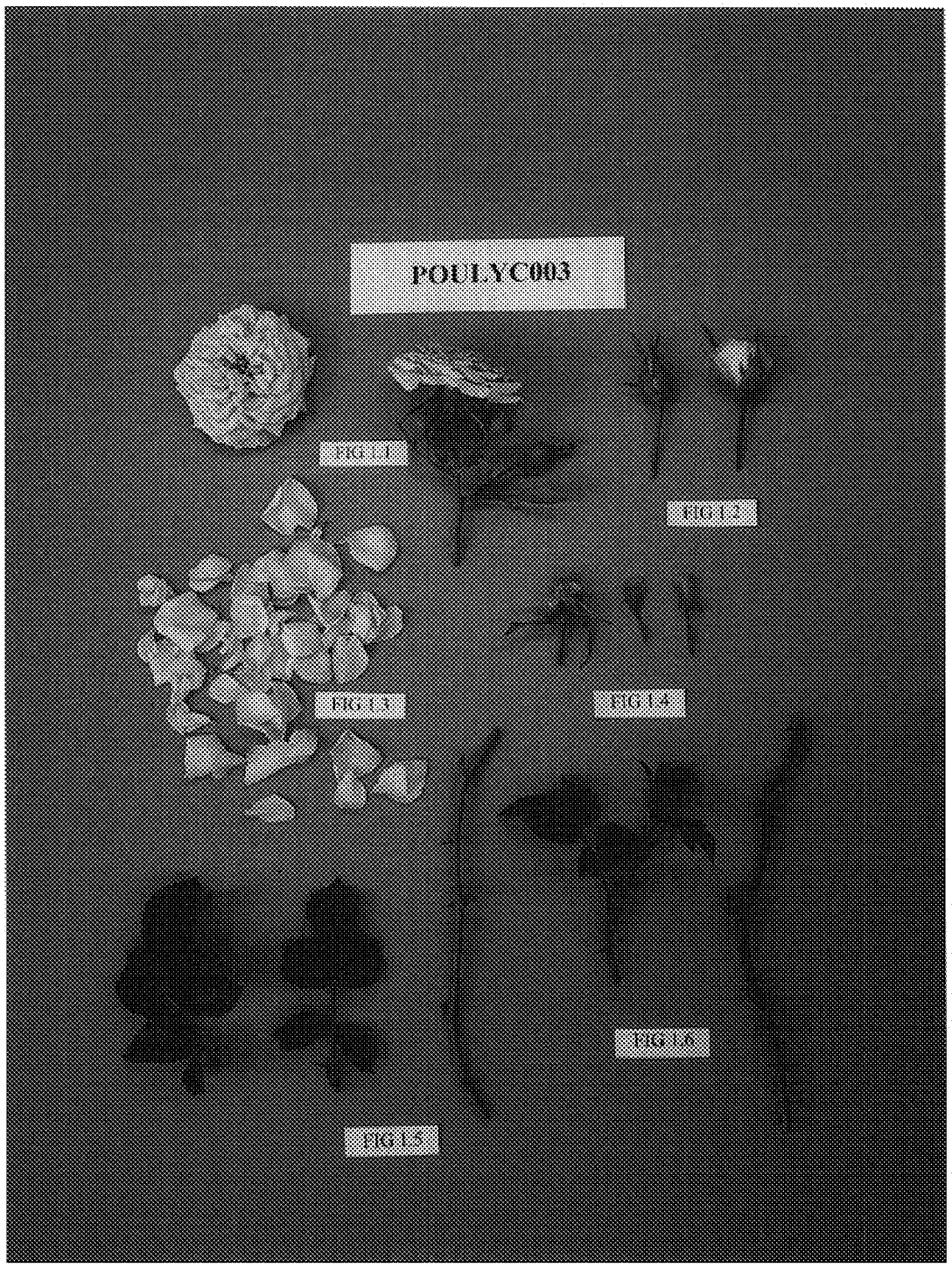

The following is a description of 'POULyc003', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULhult', a rose variety from the same inventors described and illustrated in U.S. Plant patent application Ser. No. 10/267,547 and dated Oct. 8, 2002, are compared to 'POULyc003' in Chart 1.

CHART 1

| | 'POULyc003' | 'POULhult' |
|---|---|---|
| Flower Diameter | 40 mm. | 55 to 60 mm. |
| Color of outermost petals after opening inner side. | Yellow Group 10D | Yellow Group 11D. |
| Petal Size | 20 mm (l) × 15 mm (w). | 27 mm (l) × 28 mm (w). |

Parents:

*Seed parent.*—'MEIdomonac'.

*Pollen parent.*—Unnamed seedling.

FLOWER AND FLOWER BUD

Blooming habit: Continuous.

Flower bud:

*Size.*—Upon opening, 19 mm in length from base of receptacle to end of bud.

*Bud form.*—Pointed ovoid and broad based.

*Bud color.*—As sepals unfold, petals are Yellow-Orange Group 18B with intonations of Orange Group 26C. Yellow-Orange Group 18B at ¼ opening. Sepals: Upper Surface: Color: Yellow-Green Group 144A. Lower Surface: Color: Yellow-Green Group 144A. Shape: Sepal apex is cirrhose. Base is flat at union with receptacle. Margins have medium foliaceous appendages on three of the five sepals. Size: 26 mm long by 6 mm wide.

*Receptacle.*—Surface Texture: Smooth. Shape: Funnel shaped. Size: 4 mm (h)×6 mm (w). Color: Yellow-Green Group 144A. Anthocyanin: Light. Greyed-Purple Group 184C.

*Peduncle.*—Surface: Smooth. Length: 15 to 20 mm average length. Color: Yellow-Green Group 144B. Strength: Weak.

*Borne.*—Multiples of 5 buds per flowering stem.

*Anthocyanin.*—Color: Greyed-Red Group 181B.

Flower bloom:

*Fragrance.*—Light.

*Duration.*—The blooms have a duration on the plant of approximately 10 to 14 days.

*Size.*—Average flower diameter is 40 mm when open.

*Form.*—Rosetta. Shape of flower when viewed from the side: Upon opening, upper part: Flat. Upon opening, lower part: Concave. Open flower, upper part: Flattened convex. Open flower, lower part: Very convex.

*Petalage.*—Very double. Average range: 70–80 petals under normal conditions with 30 petaloids.

Color:

*Upon opening, petals.*—Outermost petals: Outer side: Yellow Group 10D. Inner Side: Yellow Group 10D. Innermost petals: Outer side: Yellow Group 10D with intonations of Yellow-Orange Group 19A at basal and middle zones. Inner Side: Yellow Group 10D.

*Upon opening, basal petal spots.*—Outermost petals: Outer side: Yellow Group 4B. Inner Side: Yellow Group 4B. Innermost petals: Outer side: Yellow Group 4B. Inner Side: Yellow Group 4B.

*After opening, petals.*—Outermost petals: Outer side: Yellow Group 10D with light intonations of Yellow-Orange Group 14D. Inner Side: Yellow-Orange Group 14D. Innermost petals: Outer side: Yellow Group 10D with light intonations of Yellow-Orange Group 14D. Inner Side: Yellow Group 10D.

*After opening, basal petal spots.*—Outermost petals: Outer Side: Yellow Group 8B. Inner Side: Yellow Group 8B. Innermost petals: Outer Side: Yellow Group 8B. Inner Side: Yellow Group 8B.

General tonality: On open flower Yellow-Orange Group 14D. No change in the general tonality at the end of the $10^{th}$ day. Afterwards, general tonality is Yellow Group 4D.

Petals:

*Petal reflex.*—Petals reflexed strongly.

*Margin.*—Entire and uniform. Typically reflexed along margin with medium undulation of margin.

*Shape.*—Apex: Round. Base: Acute.

*Size.*—20 mm (l)×15 mm (w).

*Texture.*—Smooth.

*Thickness.*—Thin.

*Arrangement.*—Not Formal.

Petaloids:

*Quantity.*—25 to 30.

*Size.*—17 mm (l)×10 mm (w).

*Color.*—Upper Surface: Yellow Group 10D. Lower surface: Yellow Group 10D.

*Shape.*—Irregular. Oblanceolate.

Reproductive organs:

*Pistils.*—Length: 8 mm long. Quantity: 35 (actual count).

*Pollen.*—None observed.

*Anthers.*—Size: 2 mm long. Color: Yellow-Orange Group 16A. Quantity: 41 (actual count).

*Filaments.*—Color: Yellow Group 6A. Length: 4 mm.

*Stigmas.*—Superior in location to anthers. Color: Yellow-Green Group 145B.

*Styles.*—Color: Green-White Group 157A. Other intonations: At top of styles and extending into the anthers with streaks of Red-Purple Group 58B.

*Hips.*—None Observed in the field nursery in Jackson County, Oreg.

PLANT

Plant growth: Climbing habit with diminished apical dominance in flowering characteristics.

Stems:

*Color.*—Young wood: Yellow-Green Group 144A. Older wood: Yellow-Green Group 144A.

*Surface texture.*—Young wood: Smooth. Older wood: Smooth.

*Thorns.*—Incidence: 10 thorns per 10 cm of stem. Size: Average length: 5 mm. Color: Greyed-Purple Group 184C. Shape: Concave.

Plant foliage: Normal number of leaflets on normal leaves in middle of the stem: 7 leaflets.

*Compound leaf size.*—23 mm (l)×16 mm (w).

*Color.*—Mature Foliage: Upper Leaf Surface: Green Group 137C. Lower Leaf Surface: Yellow-Green Group 147C. Juvenile foliage: Upper Leaf Surface: Green Group 137C with Greyed-Purple 183A. Lower Leaf Surface: Green Group 137C with Greyed-Purple 183A. Anthocyanin: Location: Juvenile foliage and new shoots. Color: Grey-Purple Group 183A to 183D.

Plant leaves and leaflets:

*Stipules.*—Size: 17 mm. Color: Green Group 137C. Margins: Finely serrated with stipitate glands.

*Petiole.*—Length: 20 mm. Color: Yellow-Orange Group 144A. Underneath: Thorns and light pubescence observed.

*Rachis.*—Length: 20 mm. Color: Yellow-Green Group 144A. Underneath: Thorns and light pubescence observed.

*Leaflet.*—Edge: Finely serrated. Shape: General shape is Ovate. Apex is Mucronate. Base is Acute. Texture: Smooth. Arrangement: Odd pinnate. Venation: Reticulate. Glossiness: Moderate.

Disease resistance: Above average resistance to mildew, rust, black spot, and Botrytis under normal growing conditions in Jackson County, Oreg.

Cold Hardiness: The variety 'POULyc003' has been found to be cold tolerant to USDA Cold Hardiness Zone 6.

What is claimed is:

1. A new and distinct variety of rose plant of the climbing rose class, substantially as herein illustrated and described as a distinct and novel rose variety due to its abundant apricot-yellow blend flowers, disease resistance, and extended period of bloom.

* * * * *

POULYC003